(12) United States Patent
Henschel et al.

(10) Patent No.: US 12,226,642 B2
(45) Date of Patent: Feb. 18, 2025

(54) MANUFACTURING METHOD FOR AN IMPLANTABLE INTRACARDIAC DEVICE AND FOR A RESPECTIVE HEADER ASSEMBLY

(71) Applicant: BIOTRONIK SE & Co. KG, Berlin (DE)

(72) Inventors: Martin Henschel, Berlin (DE); Devan Hughes, Tualatin, OR (US); Eric Austin, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 18/549,368

(22) PCT Filed: Mar. 3, 2022

(86) PCT No.: PCT/EP2022/055388
§ 371 (c)(1),
(2) Date: Sep. 7, 2023

(87) PCT Pub. No.: WO2022/214247
PCT Pub. Date: Oct. 13, 2022

(65) Prior Publication Data
US 2024/0082587 A1 Mar. 14, 2024

Related U.S. Application Data

(60) Provisional application No. 63/172,771, filed on Apr. 9, 2021.

(30) Foreign Application Priority Data
May 12, 2021 (EP) .................................... 21173500

(51) Int. Cl.
*A61N 1/375* (2006.01)
*A61N 1/05* (2006.01)

(52) U.S. Cl.
CPC ..... *A61N 1/37512* (2017.08); *A61N 1/37518* (2017.08); *A61N 1/3754* (2013.01); *A61N 1/0573* (2013.01); *A61N 1/3756* (2013.01)

(58) Field of Classification Search
CPC ............ A61N 1/37512; A61N 1/37518; A61N 1/3754; A61N 1/0573; A61N 1/3756
See application file for complete search history.

(56) References Cited

U.S. PATENT DOCUMENTS 10,112,045 B2   10/2018   Anderson et al.
2012/0172690 A1* 7/2012   Anderson ............ A61N 1/0573
                                                          607/18

(Continued)

FOREIGN PATENT DOCUMENTS

DE    202019105583 U1   11/2019
EP         3444007 A1    2/2019

(Continued)

OTHER PUBLICATIONS

Amanat et al., "Welding methods for joining thermoplastic polymers for the hermetic enclosure of medical devices", Medical Engineering & Physics, vol. 32, Issue 7, pp. 690-699, Sep. 2010. (Year: 2010).*

(Continued)

*Primary Examiner* — Christopher W Raimund
(74) *Attorney, Agent, or Firm* — Buchanan Ingersoll & Rooney PC

(57) ABSTRACT

A manufacturing method for a header assembly for an implantable intracardiac device, wherein the header assembly comprises at least one tine extending from a conically formed base ring, further comprising a header cap and a header base, wherein the header cap and the header base each comprises a supporting side surface corresponding to the conical form of the base ring, the method comprising:

(Continued)

an assembly step, wherein the base ring is placed between the header base and the header cap such that the base ring is located adjacent the supporting header base side surface and the supporting header cap side surface, and a subsequent fixing step, wherein the header cap is permanently fixed to the header base such that the base ring is located in a base ring groove formed by the supporting header cap side surface and the supporting header base side surface.

11 Claims, 5 Drawing Sheets

(56) References Cited

U.S. PATENT DOCUMENTS

2016/0310723 A1   10/2016  Eggen et al.
2017/0106185 A1*  4/2017  Orts ..................... A61N 1/3756

FOREIGN PATENT DOCUMENTS

| EP | 3520856 A1 | 8/2019 |
| WO | 2021030392 A1 | 2/2021 |

OTHER PUBLICATIONS

International Search Report (PCT/ISA/210) and Written Opinion (PCT/ISA/237) mailed on May 24, 2022, by the European Patent Office as the International Searching Authority for International Application No. PCT/EP2022/055388. (13 pages).

* cited by examiner

MANUFACTURING METHOD FOR AN IMPLANTABLE INTRACARDIAC DEVICE AND FOR A RESPECTIVE HEADER ASSEMBLY

CROSS-REFERENCE TO RELATED APPLICATIONS

This application is the United States National Phase under 35 U.S.C. § 371 of PCT International Patent Application No. PCT/EP2022/055388, filed on Mar. 3, 2022, which claims the benefit of European Patent Application No. 21173500.6, filed on May 12, 2021, and U.S. Provisional Patent Application No. 63/172,771, filed on Apr. 9, 2021, the disclosures of which are hereby incorporated by reference herein in their entireties.

TECHNICAL FIELD

The present invention refers to an implantable intracardiac device, such as an implantable intracardiac pacemaker, and a header assembly therefor.

BACKGROUND

Active or passive intracardiac medical devices (IMD), for example implantable intracardiac pacemakers (also known as leadless pacemakers), are well known miniaturized medical devices which are entirely implanted into a heart's chamber or atrium. Intracardiac pacemakers are used for patients who suffer from a bradycardia, that is if a heart that beats too slow to fulfil the physiological needs of the patient. Intracardiac pacemakers apply electrical stimulation in the form of pulses to the heart in order to generate a physiologically appropriate heartrate and/or in the form of shocks for cardioversion or defibrillation in order to restore a more normal heart rhythm. Alternative or additional functions of intracardiac devices comprise providing other electrical or electromagnetic signals to the heart or its surrounding tissue, sensing electrical or electromagnetic signals or other physiological parameters of the heart and/or its surrounding tissue.

U.S. Publication No. 2012/0172690 A1 discloses a leadless pacemaker device which comprises a multi-piece tine fixation subassembly with a set of four remotely-deployable active fixation tines at its distal end. The document further describes a fixation of the pacemaker to a patient tissue using the four tines positioned in a circular arrangement during minimally invasive surgery. The tines are configured to penetrate into and out of a patient's tissue of the heart when deployed and positioned adjacent to this tissue in order to securely fix the device and to provide a mechanical contact of an electrode to the patient's tissue within the center of the circular arrangement of the active fixation tines. The known document further discloses a complicated manufacturing method comprising several steps for attachment of a header assembly and seven components which need to be attached to each other in order to form the header assembly. U.S. Pat. No. 10,179,236 B2 shows another example of a leadless pacemaker with a header.

In known header solutions integrated into a device having market standard device size, the header design takes space from other critical components, such as the battery or electronics module, affecting higher criticality device features, such as device longevity or therapeutic features that could have been incorporated into a larger electronics module.

Another problem consists therein that known solutions for implantable intracardiac devices contain fixation mechanisms that are either fixedly attached, axially adjustable for deployment, or contain anti-rotation features. The disadvantage of these preexisting solutions is that during acute or chronic device removal, the rotation of the device relative to the fixation mechanism is prohibited, which adds procedural challenge during the removal of the device due to varying degree of tissue encapsulation.

During manufacturing, known solutions use sophisticated alignment methods to fixate a tine array to a medical implant housing. For example, exact orienting of miniature components to each other is needed before assembly, sophisticated dispensing of adhesive material in microgram dosages or an alignment of bayonet features is needed to combine a header assembly with a device housing or to combine header assembly components. Furthermore, for the fixation of the tines complicated injection molded parts with notches are needed to receive the tines. Accordingly, the common manufacturing method can hardly be automated.

Additionally, manual cleaning may be necessary after manufacturing due to the use of silicone adhesive.

The present disclosure is directed toward overcoming one or more of the above-mentioned problems, though not necessarily limited to embodiments that do.

SUMMARY

Accordingly, there is the need for implantable intracardiac devices having smaller dimensions and at the same time providing a robust attachment mechanism and low manufacturing effort and costs which, at the same time, provides the possibility of automation.

At least the above problem is solved by a manufacturing method for a header assembly defined in claim 1, a manufacturing method for an implantable intracardiac device defined in claim 6, and by a respective header assembly defined in claim 9 and a respective implantable intracardiac device defined in claim 10.

In particular, the manufacturing method for a header assembly for an implantable intracardiac device, wherein the header assembly comprises at least one tine extending from a base ring, wherein the base ring is conically formed, further comprising a header cap and a header base, wherein the header cap and the header base each comprises a supporting side surface corresponding to the conical form of the base ring, wherein the manufacturing method comprises the following steps:

- an assembly step, wherein the base ring is placed between the header base and the header cap such that the base ring is located adjacent the supporting header base side surface of the header base and the supporting header cap side surface of the header cap, and
- a subsequent fixing step, wherein the header cap is permanently fixed to the header base such that the base ring is located in a base ring groove formed by the supporting header cap side surface and the supporting header base side surface when assembled.

The header assembly may further comprise a washer-like spacer which may form or comprise a medicament depot, for example a steroid depot in particular comprising a DXA steroid.

The implantable intracardiac device of the present invention, for example a leadless pacemaker, may comprise a cylindrical housing and a header assembly produced by the manufacturing method as described above and in further embodiments below. The cylindrical housing of the intracardiac device, the header assembly and a pin-shaped electrode have a longitudinal axis forming a longitudinal direction which runs from the proximal end to the distal end in the state after assembly. Further, the pin-shaped electrode projects from the distal end of the housing, wherein the header assembly is arranged at and attached to the distal end of the housing of the intracardiac device such that the electrode projects through the header assembly, i.e., a respective through-going or complete opening of the header assembly. The opening may be a central opening. In one embodiment, a feedthrough may be arranged around and at the proximal end of the pin-shaped electrode and may project at least partially through the opening of the header assembly.

The base ring, the header cap and the header base and, if applicable, the washer-like spacer may comprise the above described opening, wherein the size of the opening of the spacer may be such that a pin-like electrode or an electrode feedthrough located at the proximal end of the electrode may be arranged within this opening.

The header assembly is accommodated at the distal end of the intracardiac device as described in more detail above and below and provides a tine-based fixation consisting of the at least one tine. The proximal end of the header assembly is formed by the header base after the fixing of the header assembly to the intracardiac device. The header cap and the washer-like spacer may be formed separately or integrally.

In one embodiment, the header assembly comprises a plurality, in particular two, three, four, five or six tines extending from the distal end of the base ring, wherein the tines are evenly distributed along the whole circumference of the base ring. The base ring is conically formed in such way that the distal end of the base ring has a greater inner and outer diameter compared with its proximal end. The axis of the base ring extends parallel to the axis of a housing of the intracardiac device or, in other words, from the proximal to the distal direction. The at least one tine provides the fixing of the device within the heart's tissue after deployment.

The cylindrical housing of the intracardiac device comprises an electronics module having a processor, an energy source (e.g., a battery or coil (for wireless charging)) and, if applicable, a communication component such as an antenna. The processor may be adapted to process signals determined from the patient's body or received from the surrounding environment and/or to produce signals for treatment of the patient's heart. Such signals may comprise electrical stimulation in the form of pulses in order to generate a physiologically appropriate heartrate, shocks for cardioversion or defibrillation in order to restore a more normal heart rhythm and/or other electrical or electromagnetic signals to the heart or its surrounding tissue. Such signals are transformed and transmitted by the electronic module and may be applied by the pin-shaped electrode to the heart or its surrounding tissue. The pin-shaped electrode is electrically connected to the electronics module and the energy source. The hermetically sealed housing may comprise electrically conducting material, e.g., Titanium, and may function as another electrode with a regional coating, e.g., fractal Iridium, to increase the effective electrically active surface area.

The inventive manufacturing method for the header assembly advantageously enables assembly automation. Additionally, the inventive manufacturing method is very simple and therefore cost efficient because no gluing process or rotational fixing method is needed for the proposed manufacturing steps. The inventive manufacturing method comprises just uniaxial assembly ready for automation even for miniature components.

Further, the above described header assembly optimizes space due to the conical base ring and has fewer header components causing less processing and assembly steps with less costs during manufacturing of the implantable intracardiac device. The base ring is conically shaped to allow for axial height reduction while maintaining band height. The axial length and volume of the header have been minimized. When implemented into a leadless pacemaker, this improvement allows more space for other more critical features of the device, such as the battery, which would allow for increased device longevity. In other words, the space could be allotted to the electronics module, to incorporate more therapeutic features. Conversely, for the same battery and electronics module size, a reduction in header length would allow for a reduction in overall device length. This enables application for smaller patients, or alternate placement within the heart, such as the right atrium.

In one embodiment, the base ring has a plurality of notches (i.e., material cutouts, slots or other geometry), for example at least two groups of two notches arranged adjacent in circumferential direction within said base ring's distal end surface and extending from the distal side into the base ring's body. The length of one notch may be at least ¼ of the length of the base ring (i.e., its dimension into the axial direction) and maximum ⅔ of the length of the base ring. In another embodiment the length of the notch may be at least ½ of the length of the base ring. The plurality of notches allow for strain reduction during the shape setting process.

In one embodiment, each of the at least one tine comprises an abutting section directly extending from the base ring and forming a connection with the base ring and a flex zone, wherein the abutting section of the tine continues the conical form of the base ring. Each of the plurality of tines terminates at the base ring, tangent to the arc of the tines just below the surface of the header cap and the base ring is contained fully by the header cap at its distal side and by the spacer at its proximal side. The middle section of each tine of the plurality of tines has a curved form (e.g., circular curved) and the end section furthest from the base ring comprises a straight section kinked outwardly. Other forms of each tine are possible, as well. In one embodiment the base ring and the at least one tine are integrally formed. The base ring and/or the at least one tine may partially or fully consist of biocompatible material, e.g., super elastic material, for example Nitinol.

The header cap may form secure connection of at least one tine while to the housing of the intracardiac device enabling rotational freedom of the tine array (see below). Further, the header cap may provide electrical isolation of the tines from the device housing and may enable uniaxial assembly staking methods such as ultrasonic staking. The header cap has a rotation symmetrical design, e.g., approximately the form of a hollow cylinder with a supporting side surface (supporting header cap side surface) corresponding to the conical form of the base ring. This means that the size and the inclination of the supporting side surface corresponds to the size of the base ring and the taper of the base ring. The header cap may provide a flange projecting inwards from an inner surface forming a seat for the washer-like spacer, if applicable. Thereby, the header cap may provide a permanent fixing of a steroid depot at the device. Additionally, the distal end surface of the header cap may be sized and formed such that it is suitable for application of a weld horn, i.e., a relatively smooth and flat surface to allow weld horn tooling interface.

The base ring with the at least one tine is clamped and fixed against movement in longitudinal direction between the header base (on its proximal side) and the header cap (on its distal side) of the header assembly, more exactly between the supporting header base side surface and the supporting header cap side surface. The header base prevents the base ring from making contact with the device housing and from damaging any coating material (for example, Parylene) on the device housing.

The header base is radially symmetric, as well, and has the structure of a ring. One inner surface is formed as a supporting side surface (supporting header base side surface) which corresponds to the conical form of the base ring, which means that the size and the inclination of the supporting side surface corresponds to the size of the base ring and the conicity (tapering) of the base ring.

The header base as well as the header cap may comprise an electrically isolating and thermoplastic material, for example PEEK. PEEK is ideal because of its mechanical strength, biocompatibility and isolation characteristics.

According to the present invention, in the assembly step the components of the header assembly are placed adjacent to each other, namely such that the base ring is placed between the header base and the header cap such that the base ring is located adjacent to the supporting header base side surface of the header base and adjacent to the supporting header cap side surface of the header cap. In the subsequent fixing step, the header cap is permanently fixed to the header base such that the base ring is located and fully accommodated within the base ring groove formed by the supporting header cap side surface and the supporting header base side surface. Due to the conicity of the base ring and the side surfaces of header cap and header base the base ring with the tines cannot be pulled or otherwise removed from the header assembly and is permanently fixed at the header assembly. Because the base ring has a conical shape it cannot be removed out of the conical pocket formed by the supporting header cap side surface and the supporting header base side surface and is securely attached to the intracardiac device.

In one embodiment the header cap and the header base are fixed by heat staking or ultrasonic staking, or mechanical welding, for example, spin welding, stir welding, vibration welding and/or ultrasonic welding. This is realized, for example, if the header base and the header cap comprise or consist of material suitable for welding and/or staking. For application of the weld horn during the fixing step the header cap comprises a respective lateral surface at its most distal end forming an end face of suitable size. The weld horn may provide a pressing force into longitudinal direction and/or vibration in the ultrasonic range, for example with frequencies in the range of 20 kHz to 70 Hz, an amplitude between 30 mm und 50 mm, a staking force between 60 N and 100 N and a staking time up to 2 seconds, in particular up to 1.5 seconds In one embodiment each of the header base and the header cap comprises a lateral surface beside its respective supporting side surface which are located at least partially adjacent to each other after the assembly step, wherein the permanent fixing of the header cap and the header base is provided at least partially at their respective lateral surface. The lateral surface of the header base and the header cap may run at least partly parallel after the assembly step. Each lateral surface may run perpendicular, parallel to or inclined to the longitudinal axis of the header assembly or of the housing of the intracardiac device. These surfaces form staking or welding areas providing a material-to-material connection after the fixing step.

In one embodiment the header cap and/or the header base comprises a protrusion at its respective lateral surface, wherein at least a part of the material forming the protrusion is used for fixing of the header cap at the header base. Accordingly, in particular during welding the material of the protrusion melts and provides material for the permanent connection with the respective other component thereby creating a material-to-material connection (bond). In one embodiment, the respective other component may comprise an indentation opposite the respective protrusion in order to form an additional interlocking connection during the fixing step. The protrusion may be formed, for example, by single cones or elevations of other forms located at the surface of the respective lateral surface of the header cap and/or the header base, wherein at least two cones or a plurality of cones is distributed along the whole circumference of the respective lateral surface. Alternatively, the protrusion is formed as an elevated ring, having, for example, a triangular shaped cross section, located at the respective lateral surface. In one embodiment the ring, cone or elevation forms a quite sharp ridge at its top.

In one embodiment the base ring groove is sized such that the conical base ring is rotatable within the base ring groove after the fixing step relative to the housing of the intracardiac device. In one embodiment, the base ring groove is closed at its proximal end by the lateral surfaces of the header base and the header cap fixed to each other such that an inclined slot or pocket for the base ring results in which the base ring is rotatably fixed. Thereby, rotational freedom of the device relative to the fixing mechanism is provided, to enable release from the encapsulated tissue without compromising stability of the fixing mechanism, i.e., the at least one tine.

The inventive manufacturing method for an implantable intracardiac device, in particular, comprises the step that the header assembly produced by the above discussed manufacturing method is permanently attached to the intracardiac device, for example to the distal end of the housing and/or to the pin-shaped electrode or to the feedthrough, both projecting from the distal end of the housing. The completed intracardiac device has the advantages explained above with regard to the header assembly.

In one embodiment, one of the pin-shaped electrode of the intracardiac device or a feedthrough of the intracardiac device comprises at least one receiving notch, for example, forming an indentation or an undercut at its shell surface or its side surface, respectively, such that a melted section of the header cap or the header base flows into the receiving notch during the fixing step of the header assembly. The receiving notch may be formed as a ring-notch or a plurality of single notches distributed regularly or not regularly along the circumference of the respective shell surface or side surface. Thereby, during the fixing step of the header assembly, simultaneously the header assembly is fixed to the intracardiac device. The at least one receiving notch enables localized material flow to secure the header base of the header assembly to the intracardiac device housing. The melted material of the melted section realizes an interlocking connection with the pin-shaped electrode or the feedthrough. For that, the header assembly needs to be placed after or during the assembly step at the distal end of the housing of the intracardiac device such that the pin-shaped electrode and/or the feedthrough is located in the above described opening of the header assembly. In one embodiment the melted section is provided by the protrusion formed at the respective lateral surface of the header cap and/or the header base.

At least the above problem is solved by a header assembly produced using above manufacturing method or an implantable intracardiac device produced using above manufacturing method.

In one embodiment, the distal end of the housing of the intracardiac device comprises a recess with on ring-shaped protrusion at its outer circumference projecting into distal direction. The header base may be adapted to be fixed within this recess, wherein the ring-shaped protrusion forms an outer rim for the header base thereby protecting the header base after fixing the header assembly at the housing.

Further additional features may be provided by the header assembly or the intracardiac device:

The header base is used to ensure electrical isolation to the housing and to accommodate the tine array.

The header cap provides an inner diameter that has features to interact with a part of the housing implant or feedthrough flange.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The present invention will now be described in further detail with reference to the accompanying schematic drawings, wherein.

DETAILED DESCRIPTION

Figure 1:
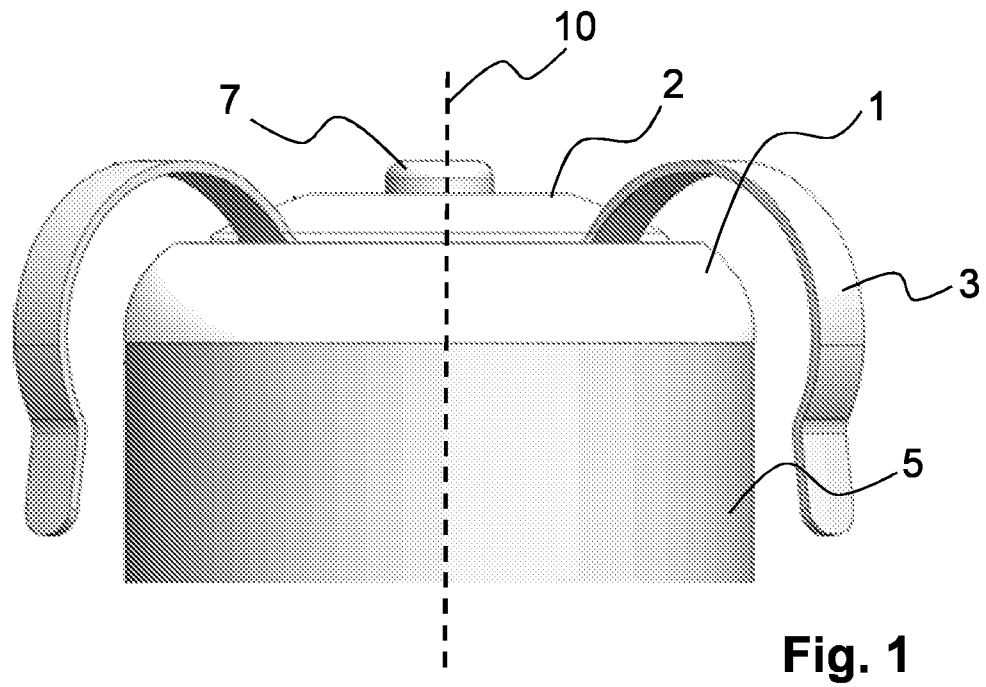
FIG. 1 shows a first embodiment of the inventive intracardiac device with the header assembly in a side view.
Figure 2:
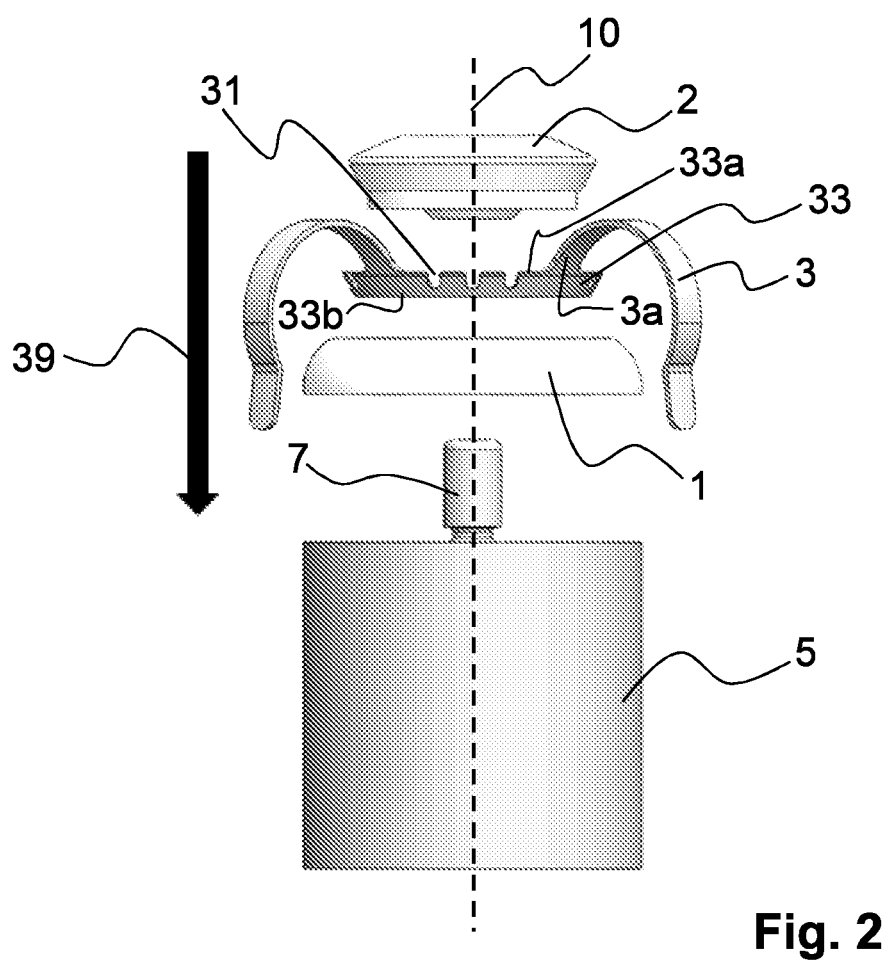
FIG. 2 shows the embodiment of FIG. 1 during assembly in a side view.

FIG. 2 illustrates an exploded view of a first embodiment of the implantable intracardiac device, e.g., a leadless pacemaker, with the header assembly, whereas FIG. 1 shows the distal end of the device after finishing the fixing step of the manufacturing method. The components are a circular ring-shaped header base 1, a basically cylindrical header cap 2, four tines formed integrally with a base ring 33, a cylindrical device housing 5, and a pin-shaped electrode 7 extending therefrom in distal direction. The common longitudinal axis 10 is shown in FIGS. 1 and 2, as well.

The base ring 33 is conically formed in such way that a distal end 33a of the base ring 33 has a greater diameter compared with its proximal end 33b.

The tines 3 extend from the conical shaped base ring 33. The base ring 33 may comprise four groups of three material relief notches (slots) 31 (only one group and part of two other groups are shown), each extending from its distal side into the base ring's 33 body to allow for shape setting of the conical base ring 33. The notches 31 are disposed over the circumference of the base ring 33 and one of the notches 31 is arranged adjacent to another one of the notches 31. Each tine has an abutting section (flex zone) 3a, a curved middle section and a straight end section (furthest from the base ring 33) kinked outwardly. The tines 3 provide the mechanical fixing of the intracardiac device within the patient's heart after deployment and penetration of the heart's tissue such that the central electrode 7 is in mechanical and electrical contact with the inner tissue of the patient's heart within one chamber or atrium.

The header base 1, the header cap 2, the base ring 33—each component comprises a central through-going opening (opening 41 of the header cap 2 and opening 51 of the header base 1—see FIG. 1) for accommodation of the electrode 7. The diameter of the central opening is such that the electrode 7 is located within this opening in the state after finishing of the manufacturing method.

The housing 5 of the intracardiac device contains a battery and an electronic module comprising a processor and ensure hermetically sealing of these components. These components are electrically connected to the electrode 7 and provide the electrical stimulation of the heart or processing of electrical signals determined from the heard. Further, the housing may contain components for communication such as an antenna. The device housing 5 of the intracardiac device may be coated with Parylene provided with a deposition process to isolate the body of the housing 5 from the electrode 7.

Figure 3:
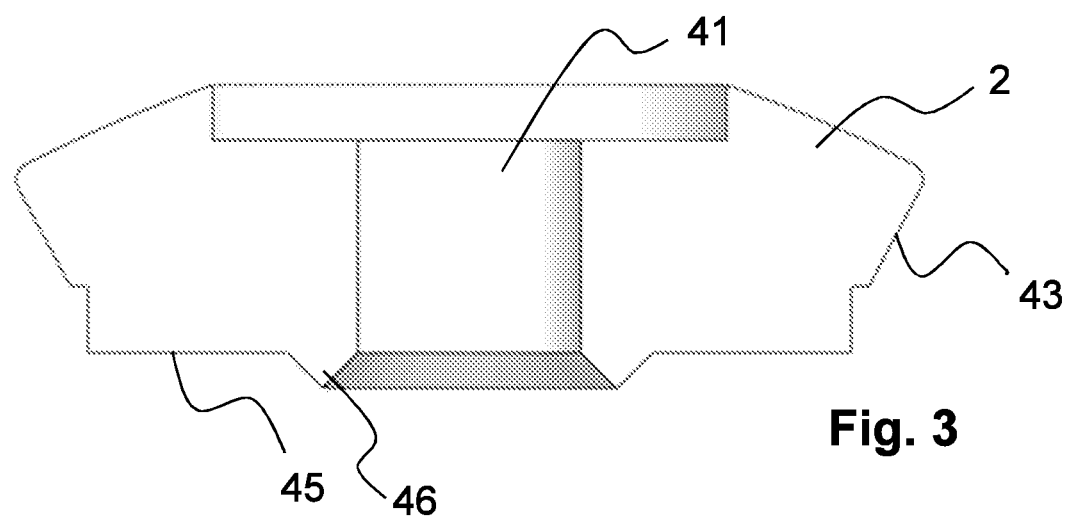
FIG. 3 depicts the header cap of the embodiment of FIG. 1 in a cross section.

The basically cylindrical, rotational symmetrical header cap 2 shown in FIG. 3 comprises the above-mentioned central opening 41 for the electrode 7, an inclined side surface 43 formed at an outer side surface of the header cap 2, a lateral surface 45 running perpendicular to the longitudinal axis 10 and a ring-shaped protrusion 46 located at the lateral surface 45 forming a ridge at its top. The ring-shaped protrusion 46 is further located adjacent the central opening 41.

Figure 4:
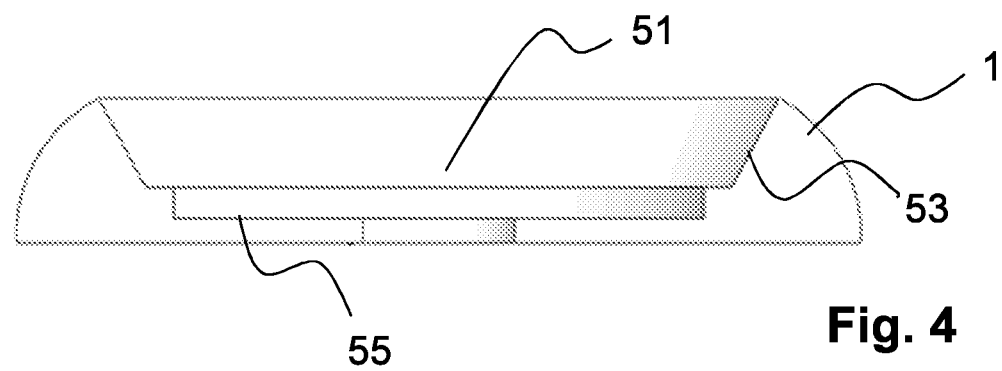
FIG. 4 shows the header base of the embodiment of FIG. 1 in a cross section.

FIG. 4 depicts the ring-shaped, radially symmetric header base 1 with its central opening 51, a lateral surface 55 and an inclined side surface 53 formed at an inner side surface of the header base 1.

Figure 6:
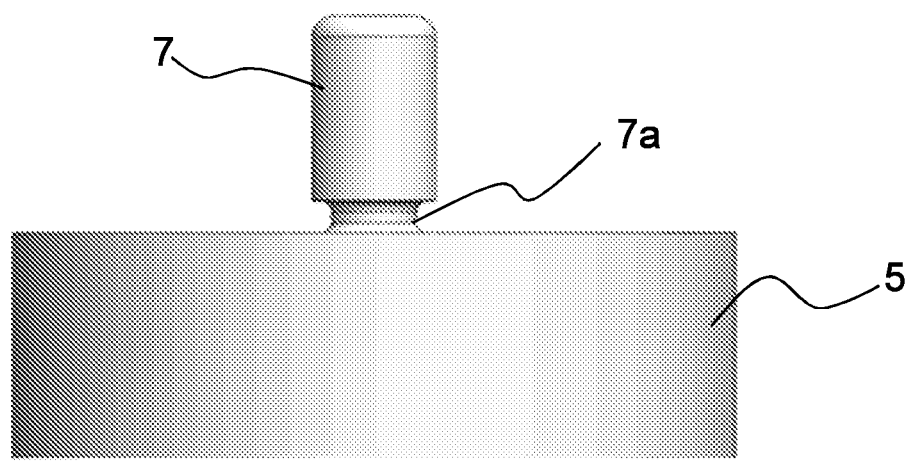
FIG. 6 shows the distal end of the housing of the intracardiac device with the pin-shaped electrode in a side view.

One can derive from FIG. 6 that the pin-shaped electrode 7 comprises a receiving notch (ring-shaped recess) 7a at its proximal end.

Figure 5:
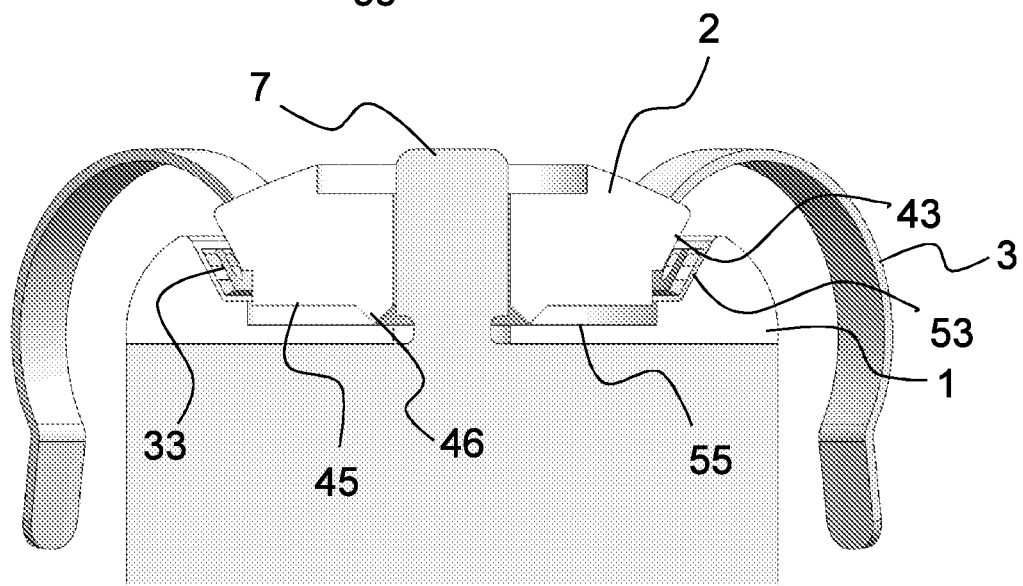
FIG. 5 depicts the embodiment of FIG. 1 during manufacturing in a cross section.

During the first step of the inventive manufacturing method for the header assembly and the intracardiac device the header cap 2, the base ring 33 with the tines 3 and the header base 2 are arranged in this order such that the supporting side surface 43 of the header cap 2 and the supporting side surface 53 of the header base 1 are located adjacent the conical base ring 33 (see FIG. 5). As shown in FIG. 2 (see arrow 39) the above-mentioned components are moved in the depicted order to the distal end of the housing 5 of the intracardiac device in order to fix the header assembly with the housing 5 and the pin-shaped electrode 7 simultaneously with the fixing of the components of the header assembly. Further, the electrode is located within the opening 41 of the header cap 2 and the opening 51 of the header base 1. Alternatively, the header assembly components may be fixed first (by fixing the header cap 2 to the header base 1 as indicated below) and afterwards to the housing 5 and the pin-shaped electrode 7. Further, at the end of the assembly step, the lateral surface 45 of the header cap 2 is located adjacent the lateral surface 55 of the header base 1. The protrusion 46 of the header cap 2 touches the opposite lateral surface 55 of the header base 1 (see FIG. 5). Further, the protrusion 46 is located close to the receiving notch 7*a* of the pin-shaped electrode 7 shown in FIG. 6.

Figure 7:
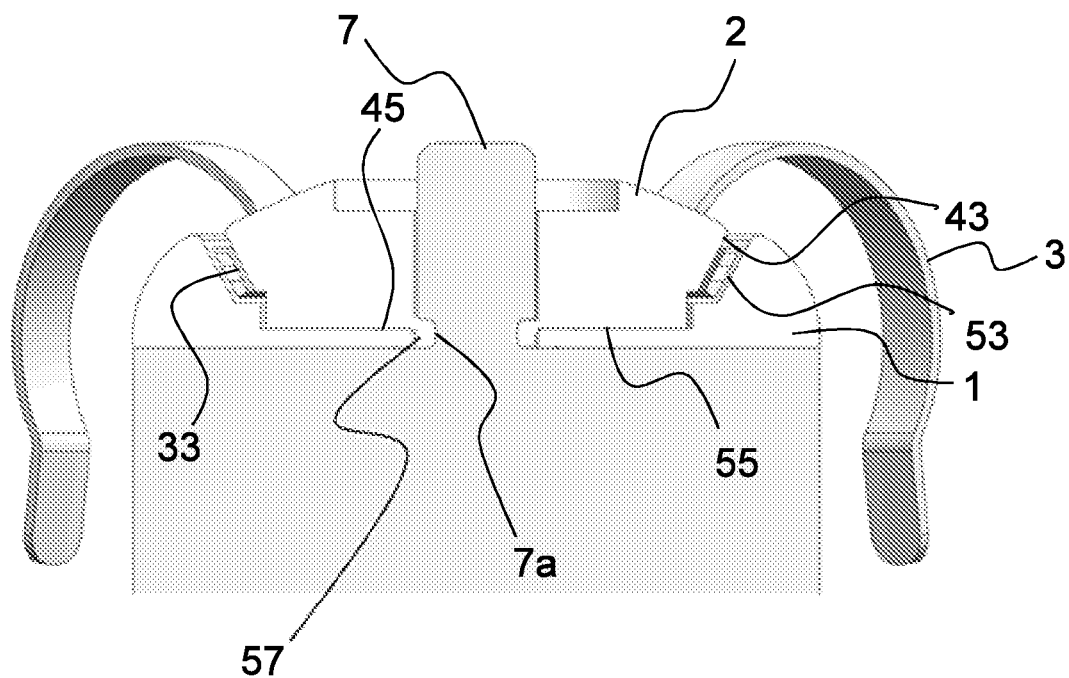
FIG. 7 depicts the embodiment of FIG. 1 after finishing of the fixing step in a cross section.
Figure 10:
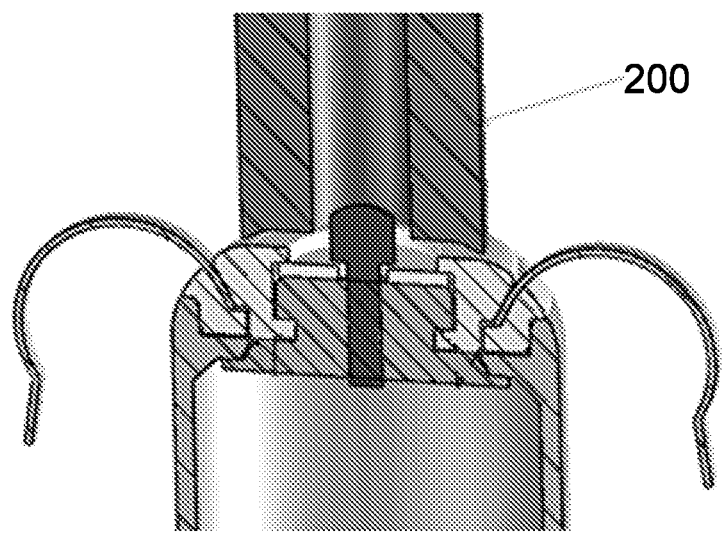
FIG. 10 depicts the embodiment of FIG. 8 during the fixing step of the manufacturing method in a cross section.

During the subsequent fixing step the components of the header assembly are permanently fixed to the housing 5 with pin-shaped electrode 7 of the intracardiac device. The resulting configuration is shown in FIG. 7. For ultrasonic welding, a sonotrode 200 may be placed at the header cap 2 as shown in FIG. 10 for the second embodiment.

The ultrasonic welding is done by pressing onto the header cap 2 comprising thermoplastic material and vibration in the ultrasonic range (typical frequencies between 20 kHz and 70 Hz). This high frequency excitation heats the thermoplastic of the header cap 2 at the interface with the header base 1 (i.e., at the lateral surfaces 45, 55 and the protrusion 46) and the thermoplastic material begins to melt. The melted plastic material begins to flow and engages with the receiving notch 7*a* provided at the pin-shaped electrode 7. After welding the plastic material of the header cap 2 and/or the header base 1 cools and solidifies at the interface between the header cap 2 and the header base 1, i.e., the lateral surfaces 45, 55 and within the receiving notch 7*a* (see reference number 57 in FIG. 7). As a result, a material-to-material and an interlocking permanent connection of the components of the header assembly and the intracardiac device housing 5 with pin-shaped electrode 7 is realized (see FIG. 7).

Further, due to the material-to-material connection of the header cap 2 and the header base 1 the lateral surfaces 45, 55 of these components form an interface thereby closing the proximal end of an inclined pocket formed by the supporting side surface 43 of the header cap 2 and the supporting side surface 53 of the header base 1 wherein the pocket fully accommodates the base ring 33. The inclined arrangement of this pocket prevents disengagement of the base ring 33 while enabling the base ring 33 and thereby the tines 3 to rotate relative to the intracardiac device housing 5 within this pocket.

The ultrasonic staking of the upper cap to the lower cap will take place at frequencies between typically 20 kHz-70 kHz. A sonotrode 200 transfers ultrasonic vibration energy into the header cap 2 (see analogously FIG. 10).

Figure 8:
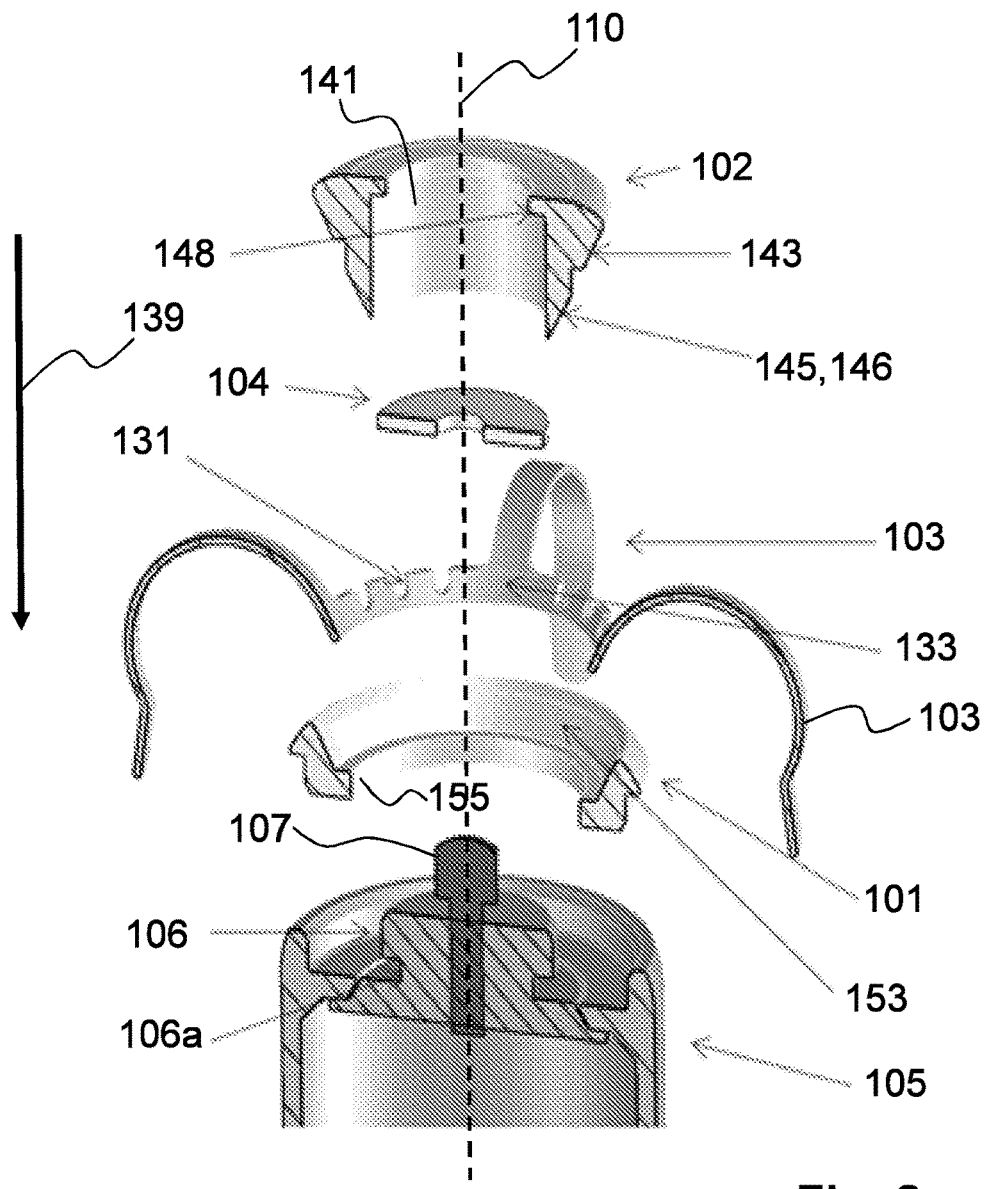
FIG. 8 shows a second embodiment of an inventive intracardiac device with header assembly in an exploded perspective view and cross section.
Figure 9:
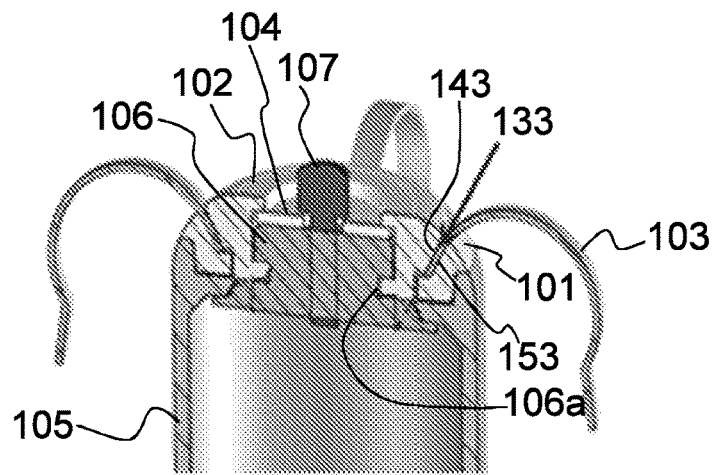
FIG. 9 shows the embodiment of FIG. 8 after finishing of the fixing step in a cross section.

A second embodiment of an intracardiac device and a header assembly is shown in FIG. 8 to 10. The most components of the intracardiac device shown in FIG. 1 to 7 and are not explained in detail again. The reference number of one component or feature of the second embodiment is just by the number 100 higher than the corresponding component or feature of the first embodiment.

However, there are some differences compared to the first embodiment, namely the intracardiac device of the second embodiment additionally comprises a feedthrough 106. The feedthrough 106 basically formed as a hollow cylinder is located at the distal end of the housing 105 of the intracardiac device and encompasses the pin-shaped electrode 107 at its proximal end. Accordingly, the receiving notch 106*a* for the melted material during welding is provided at the shell surface of the feedthrough 106. Further, the header assembly comprises a washer-like spacer 104 which may form or contain a medicament depot, for example a steroid depot. In order to fix the washer-like steroid 104, the header cap 102 comprises a flange-like protrusion 148 formed at the inner surface of the opening 141. The diameter of the electrode feedthrough 106 is greater than the diameter of the electrode 7.

The lateral surface 155 of the header base 101 runs partly parallel to the longitudinal axis 110 and partly perpendicular to this axis and is formed by an inner surface. The lateral surface 145 of the header cap 102 is formed by an outer surface running partly parallel to the longitudinal axis and partly inclined to this axis. At the most proximal end of the header cap 102 a ring-like protrusion 146 is formed having a ridge at its proximal top.

During the assembly step, the components of the header cap and the intracardiac device are arranged in a pre-defined order close to each other as indicated by arrow 139 in FIG. 9 which runs parallel to the longitudinal axis 110. The washer-like spacer 104 is arranged between the flange-like protrusion 148 of the header cap 102 and the distal end face of the feedthrough 106. Then, the subsequent fixing step is carried out as described with regard to the first embodiment above. The application of a sonotrode 200 at an end face of the header cap 102 is shown in FIG. 10. Due to ultrasonic excitation the material of the ring-like protrusion 146 is melted and flows into the receiving notch 106*a* of the feedthrough 106 thereby permanently engaging the header assembly to the intracardiac device and its housing 105. Additionally, by forming a material-to-material connection at the interface of the lateral surfaces 145, 155 an inclined pocket is formed by the supporting surfaces 143, 153 of the header cap 102 and the header base 101, respectively, for accommodation of the base ring 133. The washer-like spacer 104 is clamped by the flange-like protrusion 148 and fixed to the intracardiac device.

Figure 11:
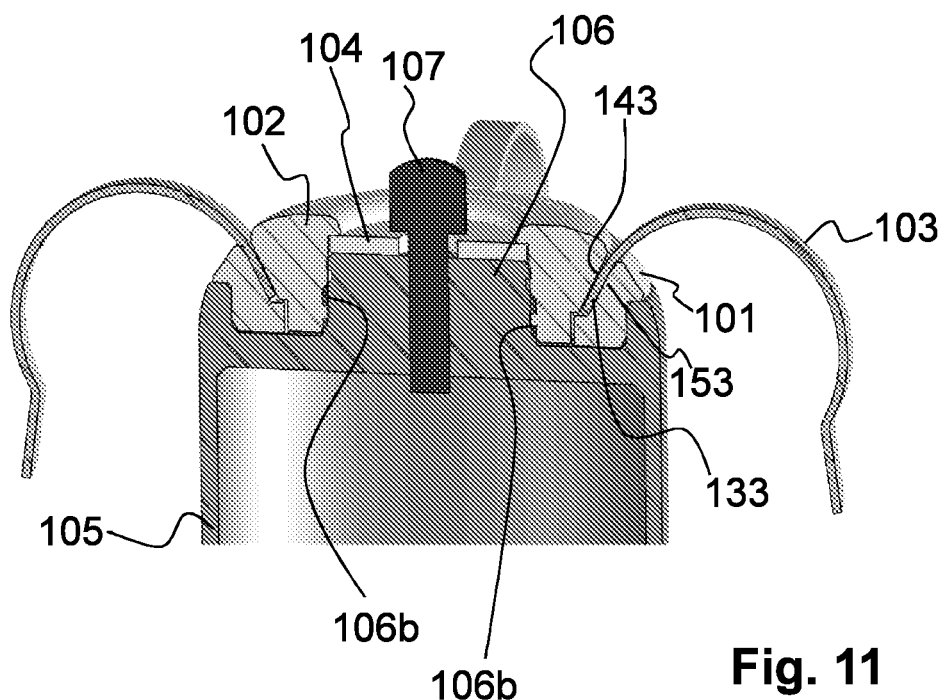
FIG. 11 shows a third embodiment of an inventive intracardiac device with header assembly after finishing of the fixing step in a cross section.

The third embodiment of an intracardiac device produced by the above explained inventive manufacturing method is shown in FIG. 11. The device is similar to the second embodiment except two (instead of one) circular grooves at the feedthrough shell surface forming two receiving notches 106*b*. Each receiving notch 106*b* is less deep than the single receiving notch 106*a*. During the fixing step, these notches 106*b* receive melted material which solidifies afterwards and provides an interlocking connection for the header assembly and the intracardiac device.

The header cap 2, 102 and the header base 1, 101 comprise PEEK or consist of PEEK or another thermoplastic material.

The above intracardiac devices with its inventive header assembly have reduced length in axial direction due to the conical shaped base ring 33, 133. It is therefore less intrusive to the mechanics of the cardiac cycle and more suitable for smaller patients and challenging situations with regard to the heart (e.g., the accommodation within a heart's atrium).

The geometry of the header assembly explained above enables simplified and automated uniaxial assembly. Additionally, the header assembly geometry enables rotational movement of the base ring 33, 133 relative to the intracardiac device housing. This is advantageous for acute or chronic device removal, when varying degrees of encapsulation are present and it is advantageous to be able to rotate the intracardiac device housing relative to the base ring 33, 133 with the at least one tine 3, 103 to free the device from the encapsulation without tearing tissue engaged in the at least one tine 3, 103.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. A manufacturing method for a header assembly for an implantable intracardiac device, wherein the header assembly comprises at least one tine extending from a base ring, wherein the base ring is conically formed, further comprising a header cap and a header base, wherein the header cap and the header base each comprises a supporting side surface corresponding to the conical form of the base ring, wherein the manufacturing method comprises the following steps:
   an assembly step, wherein the base ring is placed between the header base and the header cap such that the base ring is located adjacent the supporting header base side surface of the header base and the supporting header cap side surface of the header cap, and
   a fixing step, wherein the header cap is fixed to the header base such that the base ring is located in an inclined slot base ring groove formed by the supporting header cap side surface and the supporting header base side surface.

2. The manufacturing method according to claim 1, wherein each of the header base and the header cap comprises a lateral surface beside its respective supporting side surface which are located at least partially adjacent to each other after the assembly step, wherein the fixing of the header cap and the header base is provided at least partially at their respective lateral surface.

3. The manufacturing method according to claim 2, wherein the header cap and/or the header base comprises a protrusion at its respective lateral surface, wherein at least a part of the material forming the protrusion is used for fixing of the header cap at the header base.

4. The manufacturing method according to claim 1, wherein the base ring groove is sized such that the conical base ring is rotatable within the base ring groove after the fixing step.

5. The manufacturing method according to claim 1, wherein the header cap and the header base are fixed by heat staking, ultrasonic staking, or mechanical welding.

6. The manufacturing method according to claim 1, further comprising attaching the header assembly to the implantable intracardiac device.

7. The manufacturing method according to claim 6, wherein a pin-shaped electrode of the implantable intracardiac device or a feedthrough of the implantable intracardiac device comprises at least one receiving notch at its shell surface or its side surface, respectively, wherein attaching the header assembly to the implantable intracardiac device involves melting a section of the header cap or the header base so that the melted section flows into the receiving notch.

8. The manufacturing method according to claim 7, wherein the section is provided by a protrusion of the respective lateral surface of the header cap and/or the header base.

9. The manufacturing method according to claim 7, wherein attaching the header assembly to the implantable intracardiac device involves melting the section of the header cap so that the melted section flows into the receiving notch of the feedthrough.

10. A header assembly produced using the manufacturing method according to claim 1.

11. An implantable intracardiac device produced using the manufacturing method according to claim 6.

* * * * *